US00PP10240P

United States Patent [19]

Ilsink

[11] Patent Number: Plant 10,240

[45] Date of Patent: Feb. 17, 1998

[54] SHRUB ROSE PLANT NAMED 'INTERDUST'

[75] Inventor: Peter Ilsink, Leersum, Netherlands

[73] Assignee: Bear Creek Gardens, Inc., Medford, Oreg.

[21] Appl. No.: 760,927

[22] Filed: Dec. 6, 1996

[51] Int. Cl.[6] ..... A01H 5/00

[52] U.S. Cl. ..... Plt./1

[58] Field of Search ..... Plt./1, 8.2

*Primary Examiner*—Howard J. Locker

*Attorney, Agent, or Firm*—Klarquist Sparkman Campbell Leigh & Whinston, LLP

[57] ABSTRACT

A new and distinct variety of rose plant of the shrub class having light yellow flowers, compact spreading habit, flowers presented in clusters, small, healthy, dark green foliage, and the ability to root easily from softwood or hardwood cuttings.

1 Drawing Sheet

The present invention relates to a new and distinct variety of rose plant of the shrub class which was originated by me by crossing an unnamed seedling with an unnamed seedling.

The primary objective of this breeding was to produce a new rose variety having the yellowish flowers (yellow eye with orange red outer color) clustering flower habit and compact growth of the female parent combined with the healthy dark green foliage and spreading growth of the male parent. The objective was substantially achieved, along with other desirable improvements, as evidenced by the following unique combination of characteristics that are outstanding in the new variety and that distinguish it from its parents, as well as from all other varieties of which I am aware:

1. Light yellow flowers;
2. Compact spreading habit;
3. Flowers presented in clusters;
4. Small, healthy, dark green foliage; and
5. Ability to root easily from softwood or hardwood cuttings.

Asexual reproduction of this new variety by softwood and hardwood cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—Unnamed seedling.

Classification:

*Botanical.*—Shrub.

*Commercial.*—*Rosa hybrida.*

Flower

Observations made from specimens grown in a garden environment at Somis, Calif., in January through September, 1996.

Blooming habit: Continuous

Bud:

*Size.*—½ inch long when the petals start to unfurl.

*Form.*—The bud form is short, pointed ovoid.

*Color.*—When sepals first divide, bud color is Yellow Group 6D. When half blown, the upper sides of the petals are Yellow Group 6D; and the lower sides of the petals are Yellow Group 6D.

*Sepals.*—Color: Green Group 138C. Surface texture: Covered in fine hairs. There are three lightly appendaged sepals. There are two unappendaged sepals with hairy edges.

*Receptacle.*—Color: Green Group 137D. Shape: Apple. Size: Small (5/32 inch×5/32 inch). Surface: Smooth with a few very fine hairs.

*Peduncle.*—Length: Short (¾ inch). Surface: Glandular (very fine glands). Color: Light green and bronzy. Strength: Stiff, erect.

Bloom:

*Size.*—Small. Average open size is 1½ inches.

*Borne.*—Several together, in clusters. If in clusters: flat.

*Stems.*—Short. Average length is about 8 inches to 12 inches.

*Form.*—When first open: Cupped. Permanence: Flattens.

*Petalage.*—Number of petals under normal conditions: 5 to 10.

*Color.*—The upper side of the petals is Yellow Group 6D. The reverse side of the petals is Yellow Group 6D. The base of petals has very small (1/32 inch×1/32 inch) deep yellow (Yellow Group 6A) half moon at the point of attachment. The major color on the upper side is Yellow Group 6D.

*Variegations.*—None.

*Discoloration.*—The general tonality at the end of the first day: No change. At the end of the third day: General fading to near Yellow Group 4D.

*Fragrance.*—Slight.

Petals:

*Texture.*—*Thick.*

*Shape.*—Deltoid.

*Form.*—Flat.

*Arrangement.*—Imbricated, with few petaloids in the center.

*Persistence.*—Drop off cleanly.

*Lastingness.*—On the plant: Short (3 to 4 days). As a cut flower: Not tested.

Reproductive parts:

*Anthers.*—Size: Small. Quantity: Many. Color: Yellow. Arrangement: Regular around styles.

*Filaments.*—Color: Yellow.
*Pollen.*—Color: Gold yellow.
*Styles.*—Color: Greenish white.
*Stigmas.*—Color: Greenish white.

Form: Shrub.

Growth: Dwarf. Vigorous, sprawling and compact. Plant on its own roots at one year of age is between about 12 inches to 16 inches tall and 24 inches to 30 inches wide.

Foliage:
*Number of leaflets on normal mid-stem leaves.*—5 or 7 (mostly 7).
*Size.*—Small (3 inches×1½ inches.
*Quantity.*—Abundant.
*Color.*—New foliage: Greyed Purple Group 183A but very quickly turns green. Old foliage: Upper surface: Green Group 139A. Lower surface: Green Group 139C.

Leaflets:
*Shape.*—Pointed oval.
*Texture.*—Upper side: Leathery, glossy.
*Edge.*—Serrated.
*Serration.*—Single, small.
*Petiole Rachis.*—Color: Reddish when young but turns green as plant ages.
*Petiole Underside.*—Rough, with prickles and glands along the side of the petiole.
*Stipules.*—Long and narrow; serrated with glands.
*Disease resistance.*—Resistant to mildew and rust under normal growing conditions at Somis, Calif.

Wood:
*New wood.*—Color. Reddish. Bark: Smooth
*Old wood.*—Color: Green. Bark: Smooth.

Prickles:
*Quantity.*—On main canes from base: Ordinary. On laterals from main canes: Ordinary.
*Form.*—Short (3/32 inch) .
*Color when young.*—Red.

Small prickles:
*Quantity.*—On main stalks: None. On laterals: None.

I claim:

1. A new and distinct variety of rose plant of the shrub class, substantially as herein shown and described, characterized particularly as to novelty by the unique combination of its light yellow flowers, compact spreading habit, flowers presented in clusters, small, healthy, dark green foliage, and the ability to root easily from softwood or hardwood cuttings.

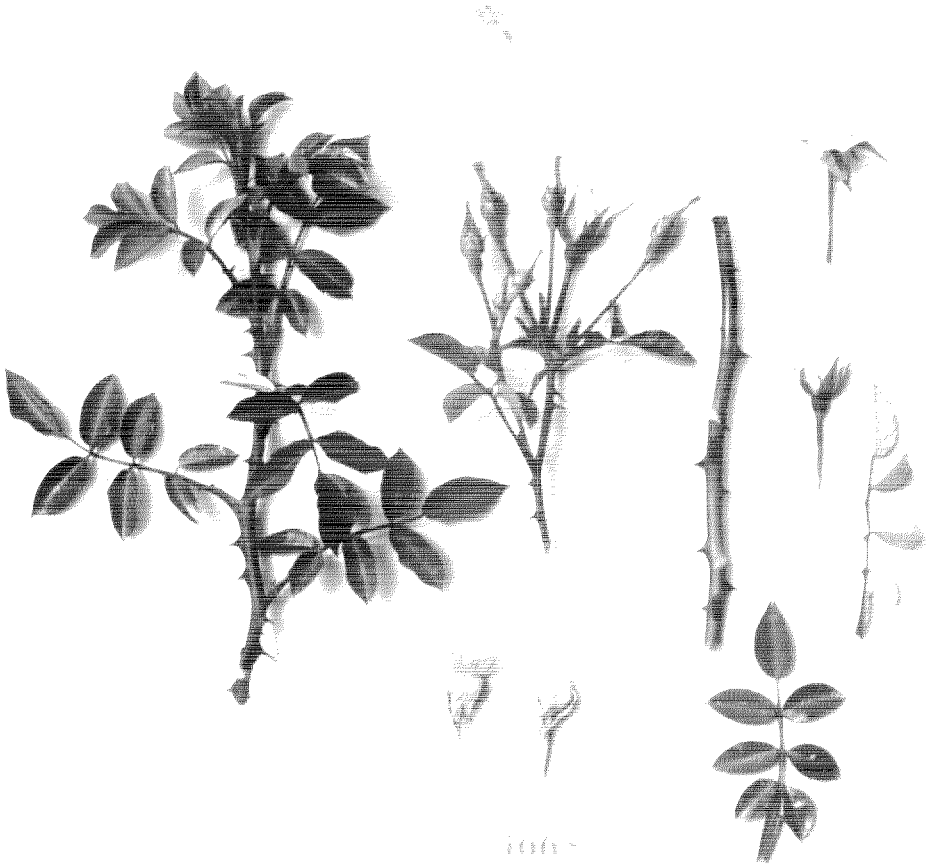

* * * * *